United States Patent [19]

Shimamoto et al.

[11] Patent Number: 4,493,938
[45] Date of Patent: Jan. 15, 1985

[54] METHOD FOR THE PRODUCTION OF THIOALKYLENE GLYCOLS

[75] Inventors: Kunihiro Shimamoto, Otsu; Hiroshi Hatanaka, Takasago; Shinichiro Seki, Otsu; Ryozo Orita, Himeji, all of Japan

[73] Assignee: Toyo Kasei Kogyo Co., Ltd., Osaka City, Japan

[21] Appl. No.: 253,144

[22] Filed: Apr. 10, 1981

[30] Foreign Application Priority Data

Apr. 15, 1980 [JP] Japan .................................. 55-49745

[51] Int. Cl.$^3$ .................. C07C 149/00; C07C 148/04
[52] U.S. Cl. ......................................... 568/62; 568/69
[58] Field of Search ................................... 568/69, 62

[56] References Cited

FOREIGN PATENT DOCUMENTS 42-20522 10/1967 Japan .................................... 568/69

OTHER PUBLICATIONS

Robertson, et al., Laboratory Practice of Organic Chemistry, 4th Edition, MacMillan Company, New York, 1962, pp. 201, 202.

Fieser, Experiments in Organic Chemistry, 2nd Edition, D. C. Heath & Company, New York, 1941, pp. 184–185.

*Primary Examiner*—Alan L. Rotman
*Assistant Examiner*—Robert C. Whittenbaugh
*Attorney, Agent, or Firm*—Wenderoth, Lind & Ponack

[57] ABSTRACT

This invention is concerned with a method for the production of thioalkylene glycols by using the reaction solvent containing mainly the thioalkylene glycol, the product of the reaction of alkylene oxide and hydrogen sulfide, without using any other special solvent or inert solvent, in the presence of anion exchange resin as the catalyst, the method which enables the simple, economical and high-yield production of thioalkylene glycols because a high pressure is not necessarily required and the purification and isolation are carried out very easily.

For example, according to this invention, thioethylene glycol was obtained in a 91% yield from ethylene oxide and hydrogen sulfide in the mixture of thioethylene glycol and thiodiethylene glycol as the solvent in the presence of the anion exchange resin as the catalyst. Similarly, thiopropylene glycol in a 95% yield from propylene oxide and hydrogen sulfide in thiopropylene glycol as the solvent, and thio-α-butylene glycol in a 94% yield from α-butylene oxide and hydrogen sulfide in thio-α-butylene glycol as the solvent, were obtained.

7 Claims, No Drawings

METHOD FOR THE PRODUCTION OF THIOALKYLENE GLYCOLS

DETAILED DESCRIPTION OF THE INVENTION

This invention is concerned with a method for the simple, economical and high-yield production of thioalkylene glycols from alkylene oxides and hydrogen sulfide, using the reaction solvent containing mainly thioalkylene glycol, the reaction product but without using any other special solvent or inert solvent, in the presence of the anion exchange resin as the catalyst.

Various methods have been known so far for the production of thioalkylene glycols from hydrogen sulfide and alkylene oxides. For example, (a) The method in which hydrogen sulfide is sufficiently dissolved in thiodiglycol and then ethylene oxide is introduced to produce monothioglycol and/or thiodiglycol (Japanese published examined patent application No. 19783/1964). According to this method the reaction rate is so slow that it is not suitable for industrialization and, in addition, thiodiglycol of as much as 71.9% in the reaction solution needs to be recovered.

(b) The method in which, in the presence of bis-($\beta$-hydroxylthyl)-thioether, e.g. thiodiglycol, as the solvent, ethylene oxide and hydrogen sulfide in the molar ratio of 1:1 are allowed to react at a high temperature and a high pressure to produce thioethylene glycol (Japanese published examined patent application No. 35047/1973). This method has the defect that reaction should be carried out under high pressure and thiodiglycol of about 40% should be recovered.

(c) The method in which alkylene oxide and hydrogen sulfide are mixed under the pressure of 1 to 15 atm at 20° to 100° C. and allowed to react in finely divided state by using a tubular stirrer to produce thioalkylene glycols (Japanese published unexamined patent application No. 13518/1972). This method is neither general nor industrial because it requires a special reaction apparatus.

(d) The method in which a mixture of hydrogen sulfide and alkylene oxide, especially the one which contains 2 to 4 carbon atoms in a molecule, is passed through a catalyst bed consisting of ion exchange resin to produce thioalkylene glycol (Japanese published examined patent application No. 20522/1967). According to this method, the reaction needs to be carried out at a very low rate of the supply of the materials because the removal of the reaction heat is difficult. Therefore the production efficiency is low and industrialization is difficult. In the Japanese published examined patent application No. 20522/1967 described above, an example, in which the material gases diluted with an inert gas are introduced to the ion exchange resin tower, is also described, but even in this procedure the efficiency of the removal of reaction heat is not different so much from that in the procedure described above; the production efficiency is still low and there are some problems in the recovery and re-utilization of the unreacted material gases.

The inventors have studied in earnest how to overcome the defects of the conventional methods described above and finally obtained this invention which enables the simple and high-yield industrial production of the aimed products; this invention provides a method in which alkylene oxide and hydrogen sulfide are allowed to react in the solvent containing thioalkylene glycol, the reaction product, as the main constituent, in the presence of anion exchange resin as the catalyst to produce thioalkylene glycol.

According to this invention thioalkylene glycols may be produced in such a way that the reaction solvent and the catalyst are put into a reactor equipped with a stirrer, the system is saturated with hydrogen sulfide, and then alkylene oxide is added to react with hydrogen sulfide. However the anion exchange resin catalyst is generally apt to be broken by stirring, and so it is desirable to use the catalyst at rest. Therefore in the industrial practice, a solvent-circulating production process is desirable in which the anion exchange resin is packed in a reaction tower, to which the mixture or solution of alkylene oxide and hydrogen sulfide is supplied to produce thioalkylene glycols.

The solvent circulating process may be used both for batch- and for continuous operation. In this process a certain amount of the reaction solution is circulated to the reaction tower and the excess amount of the solvent equivalent to the amount produced is intermittently or continuously taken out as the product.

The reaction equations including that of the side reaction in the synthesis of thioalkylene glycol from alkylene oxide and hydrogen sulfide according to this invention are shown in (1) and (2).

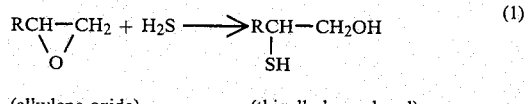

(alkylene oxide)   (thioalkylene glycol)

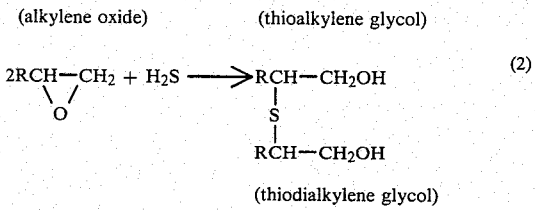

(thiodialkylene glycol)

(where R denotes H or an alkyl group of $C_1$ or $C_2$).

As can be seen from the equations (1) and (2), the yield of thioalkylene glycol is expected to be dependent on the concentration of hydrogen sulfide dissolved. This was confirmed by the study by the inventors: it was found that, at least at a temperature in the range of 5° to 80° C. and at an absolute pressure in the range of 1 to 10 kg/cm², the yield of thioalkylene glycol may be approximately expressed as a function of the concentration of dissolved hydrogen sulfide.

That is, the reaction temperature and the reaction pressure exert their main influence on the yield of thioalkylene glycol not directly but indirectly through the concentration of dissolved hydrogen sulfide.

Because the concentration of dissolved hydrogen sulfide decreases as the temperature is increased and increases as the pressure is increased, the yield of the product is, in general, higher at a lower temperature if the pressure is constant and higher at a higher pressure if the temperature is constant.

The reaction temperature affects directly the reaction rate and therefore a temperature in the range of 0° to 100° C. may be appropriate. If the temperature is too low, the reaction rate will be very small, i.e. the process will be economically disadvantageous. If the temperature is above the limit temperature for the use of the anion exchange resin, the catalyst needs to be exchanged often, i.e. the process is not economical because of the cost and the labor for the exchange.

The reaction pressure is also dependent on the operation temperature; e.g. at 5° C. a good yield may be obtained even at an ordinary pressure, but at 60° C. a pressure of around 10 kg/cm$^2$ is desirable. When thioalkylene glycol and thio-di-alkylene glycol are produced simultaneously, the reaction temperature and pressure should be selected according to the ratio of the products.

The inventors confirmed that the molar ratio of the hydrogen sulfide and alkylene oxide supplied does not affect the yield, and therefore attention should be paid only to maintain the fixed pressure of hydrogen sulfide while alkylene oxide is supplied at a fixed rate. Thioalkylene glycol, the main reaction product, is used as the reaction solvent and it does not matter that thiodialkylene glycol, the by-product, is included.

The amount to be used and the circulating rate may be such that the reaction system can be maintained at constant temperature by releasing the reaction heat out of the system.

That is, because the reaction of hydrogen sulfide and alkylene glycol releases a large quantity of heat, the amount of thioethylene glycol as the solvent, the reaction product, and the circulating rate should be large enough to control the reaction temperature.

That is, when an anion exchange resin packed tower is used in the production, the circulating rate of the solvent into the said packed tower should be selected so that the temperature at the inlet may not become very different from that at the outlet. If the temperature and the pressure can be maintained constant, the yield is not affected even if the flow-rate is changed.

Among various anion exchange resins, weakly basic or strongly basic anion exchange resins may be used: primary, secondary and tertiary amine derivatives, polyamines of styrene-divinylbenzene copolymer, and quaternary ammonium salt derivatives of styrene polymer and methacrylresin may be used.

For example, Amberlite IRA-45 (trade name) i.e. polyamine of polystyrene, Duolite A-2 (trade name) i.e. polyamine of phenol resin, or Duohite A-161 (trade name) i.e. quaternary ammonium salt derivative of polystyrene etc. is preferrably used.

At the beginning of the reaction according to this invention, it is desirable that the solvent is sufficiently saturated with hydrogen sulfide under the prescribed condition, followed by the addition of alkylene oxide liquid or gas to initiate the reaction.

If the reaction has been initiated by the addition of alkylene oxide before hydrogen sulfide is dissolved to saturate the solvent, the yield of thioalkylene glycol will be low while the yield of thiodialkyl glycol, the by-product, will be high.

Of course in this case, if the reaction time is prolonged, the yield increases until the desired yield may be obtained.

If unreacted alkylene oxide remains in the reaction solution to be taken out from the reaction system, it is desirable that the reaction mixture is introduced to another anion exchange resin tower so that alkylene oxide is allowed to react completely, then hydrogen sulfide dissolved is recovered, and thioalkylene glycol may be obtained as the product.

Otherwise, after both hydrogen sulfide and alkylene oxide react until they are consumed completely, the reaction product may be taken out from the reaction system. If the concentration of thiodialkylene glycol is too high for the purpose of the use of thioalkylene glycol, or if both thioalkylene glycol and thiodialkylene glycol are desired, the two substances are separated by distillation before use.

The advantages of this invention may be summarized as follows.

(i) The yield of thioalkylene glycol produced according to this invention is high. For example, the yield of thioethylene glycol is as high as 97% on the basis of the amount of ethylene oxide used.

(ii) The production efficiency per unit volume of the reaction tower is high. For example, 4.8 kg thioethylene glycol is obtained per l of the volume of the anion exchange resin packed tower after 8 hr of reaction time (0.6 kg/hr, l), the yield being considerably high as compared with 0.02 to 0.06 kg/hr, l by a common organic synthetic reaction.

(iii) Waste gas, which is derived from the material gas unabsorbed in the solvent and is released directly from the reaction system, is not produced. If the unreacted alkylene oxide gas is released from the reaction system, such problems as its recovery and re-utilization will arise but there is no such problems in the process according to this invention.

(iv) Seperation of the reaction solution from the catalyst is not necessary because the solid anion exchange resin is used as the catalyst.

(v) Seperation of the product from the solvent is not necessary because thioalkylene glycol, the main reaction product, is used as the reaction solvent, and a crude reaction product containing thioalkylene glycol at a high concentration can be obtained.

(vi) Because the reaction of hydrogen sulfide and alkylene oxide used in this invention releases a large quantity of heat, generally a special reaction apparatus is required to remove the reaction heat when the reaction is carried out in the gas phase or the production efficiency per unit volume of the reaction tower is small. However, according to this invention, sufficiently much reaction solvent may be used and therefore the reaction temperature may very easily be controlled, which enables a stable operation.

(vii) Because of the high yield of thioalkylene glycol, a high pressure (more than 10 kg/cm$^2$ of the gauge pressure) is not necessarily required. A good yield is attained at a low pressure, which enables a simple operation.

(viii) The mixture of the products after removal of hydrogen sulfide consists essentially only of thioalkylene glycol and thiodialkylene glycol and does not contain any other by-product or polymerized alkylene oxide etc.; therefore the purification and separation may be carried out very easily.

In the following this invention is to be explained with examples.

EXAMPLE 1

To the reaction tower packed with 300 ml of anion exchange resin (Amberlite IRA-45, OH form), the solvent, the mixed solution of 93% of thioethylene glycol and 7% of thiodiethylene glycol of which temperature has been adjusted to 5° C. is supplied by circulating at the flow rate of 6 l/hr, hydrogen sulfide is supplied to the solvent in such a way that the pressure in the system may be maintained at 0.1 kg/cm$^2$ (gauge pressure), and the state that the solvent is steadily saturated with hydrogen sulfide should be maintained.

To this reaction system 200 g of ethylene oxide is supplied at 10 g/hr and allowed to react. The reaction is continued until the unreacted ethylene oxide is completely consumed and then stopped.

Analysis of the reaction solution showed that it contains 93% of thioethylene glycol and 7% of thiodiethylene glycol, the yield of thioethylene glycol being 91% on the basis of the amount of ethylene oxide used.

EXAMPLE 2

To the reaction tower packed with 182 ml of anion exchange resin (Amberlite IRA-45, OH form), the solvent, the mixture of 97.7% of thioethylene glycol and 2.3% of thiodiethylene glycol of which temperature has been adjusted to 40° C. is supplied by circulating at the flow rate of 6 l/hr, and hydrogen sulfide is supplied in such a way that the pressure in the system of 9 kg/cm$^2$ (gauge pressure) may be maintained, so that the state that the solvent is steadily saturated with hydrogen sulfide should be maintained.

To this reaction system 200 g of ethylene oxide is supplied at 62 g/hr, allowed to react 1 more hour to consume the unreacted ethylene oxide, and the reaction is stopped.

The analysis of the reaction solution after removal of hydrogen sulfide showed that it consisted of 97.7% of thioethylene glycol and 2.3% of thiodiethylene glycol, the yield of thioethylene glycol being 97% on the basis of the amount of ethylene oxide used.

EXAMPLE 3

When the reaction was carried out similarly to the procedure described in Example 2 although the pressure in the system was 5 kg/cm$^2$ (gauge pressure) and thiopropylene glycol instead of thioethylene glycol and thiodiethylene glycol, and propylene oxide instead of ethylene oxide were used, the yield of thiopropylene glycol being 95% on the basis of the amount of propylene oxide used.

EXAMPLE 4

When the reaction was carried out similarly to the procedure described in Example 2 although the pressure in the system was 5 kg/cm$^2$ (gauge pressure) and thio-α-butylene glycol, instead of thioethylene glycol and thiodiethylene glycol and α-butylene oxide instead of ethylene oxide were used, the yield of thio-α-butylene glycol was 94% on the basis of the amount of α-butylene oxide used.

We claim:

1. A method for the production of thioalkylene glycols which consists essentially of introducing hydrogen sulfide into a reaction system containing a reaction solvent containing mainly a thioalkylene glycol, which is the same as the thioalkylene glycol produced, and an anion exchange resin as a catalyst, said hydrogen sulfide being introduced in amounts sufficient to saturate the thioalkylene glycol solvent and then introducing alkylene oxide in amounts sufficient to react with the hydrogen sulfide to produce the objective thioalkylene glycol, said hydrogen sulfide being maintained in the reaction system in amounts sufficient to saturate the thioalkylene glycol solvent as well as to react with the alkylene oxide and wherein the reaction is carried out at a temperature in the range of 0° to 100° C. and at a pressure in the range of 1 to 10 kg/cm$^2$, said reaction solvent being used in amounts sufficient to remove the heat of reaction from the reaction system, thus controlling the reaction temperature so as to operate the system under relatively constant and stable reaction temperature conditions.

2. A method according to claim 1 in which the alkylene oxide and hydrogen sulfide in the solvent containing mainly thioalkylene glycol are reacted in a reaction tower packed with an anion exchange resin, and the reaction solution thus-obtained is circulated throughout the reaction tower to be used as a reaction solvent; and wherein any excess amount of solvent equivalent to the amount produced by the reaction is intermittently or continuously removed from the reaction tower; said circulation of the reaction solvent throughout the reaction tower being at such a rate as to remove the heat of reaction and to control the temperature such that the reaction system may be operated under stable and relatively constant temperature conditions.

3. A method according to claims 1 or 2 in which the anion exchange resin is a weakly basic resin.

4. A method according to claims 1 or 2 in which the anion exchange resin is a strongly basic resin.

5. A method for the production of thioalkylene glycols according to claims 1 or 2 in which the thioalkylene glycol produced is thioethylene glycol and in which thioethylene glycol is used as the solvent and ethylene oxide is the alkylene oxide reactant.

6. A method according to claims 1 or 2 in which the thioalkylene glycol produced is thiopropylene glycol, the solvent is thiopropylene glycol and the alkylene oxide reactant is propylene oxide.

7. A method according to claims 1 or 2 in which the thioalkylene glycol produced is thio-α-butylene glycol, the solvent is thio-α-butylene glycol and α-butylene oxide is the alkylene oxide reactant.

* * * * *